US011426117B2

(12) United States Patent
Neumann

(10) Patent No.: US 11,426,117 B2
(45) Date of Patent: Aug. 30, 2022

(54) METHODS AND SYSTEMS FOR DIETARY COMMUNICATIONS USING INTELLIGENT SYSTEMS REGARDING ENDOCRINAL MEASUREMENTS

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 0 days.

(21) Appl. No.: 17/136,095

(22) Filed: Dec. 29, 2020

(65) Prior Publication Data
US 2022/0202351 A1   Jun. 30, 2022

(51) Int. Cl.
*A61B 5/00* (2006.01)
*G06N 3/08* (2006.01)
(Continued)

(52) U.S. Cl.
CPC .......... *A61B 5/4227* (2013.01); *A61B 5/6801* (2013.01); *A61B 5/7275* (2013.01);
(Continued)

(58) Field of Classification Search
CPC .. G06Q 50/22–24; G16H 20/60; G16H 50/30; A61B 5/42; A61B 5/4227
See application file for complete search history.

(56) References Cited

U.S. PATENT DOCUMENTS

| 5,527,788 A | 6/1996 | Svec et al. |
| 8,388,530 B2 * | 3/2013 | Shusterman ........... G16H 50/70 600/509 |

(Continued)

FOREIGN PATENT DOCUMENTS

| CH | 713713 | 10/2018 |
| CN | 103667456 | 3/2014 |

(Continued)

OTHER PUBLICATIONS

S.B. Kotsiantis, "Supervised Machine Learning: A Review of Classification Techniques", Jul. 16, 2007, Informatica 31 (2007) 249-268, all pages. (Year: 2007).*
(Continued)

*Primary Examiner* — Jason S Tiedeman
*Assistant Examiner* — Jessica Marie Webb
(74) *Attorney, Agent, or Firm* — Caldwell Intellectual Property Law

(57) ABSTRACT

A system for dietary communications using intelligent systems regarding endocrinal measurements includes a computing device designed and configured to obtain a first endocrinal measurement relating to a user; compare the first endocrinal measurement to an endocrinal system effect; generate a body dysfunction label for the first endocrinal measurement as a function of the endocrinal system effect; identify a dietary communication as a function of the body dysfunction label, the first endocrinal measurement, and a first machine learning process, the first machine learning process trained using a first training set relating endocrinal measurements and body dysfunction labels to dietary communications; and present the dietary communication.

16 Claims, 9 Drawing Sheets

(51) Int. Cl.
*G16H 50/30* (2018.01)
*G16H 20/60* (2018.01)

(52) U.S. Cl.
CPC .............. *G06N 3/08* (2013.01); *G16H 20/60* (2018.01); *G16H 50/30* (2018.01)

(56) References Cited

U.S. PATENT DOCUMENTS

| | | | |
|---|---|---|---|
| 9,974,903 B1* | 5/2018 | Davis | A61B 5/742 |
| 10,055,549 B2* | 8/2018 | Chung | G16H 50/20 |
| 10,154,460 B1* | 12/2018 | Miller | A61B 5/1455 |
| 10,559,386 B1* | 2/2020 | Neumann | G06N 20/10 |
| 10,832,172 B1* | 11/2020 | Neumann | G16H 40/67 |
| 10,922,995 B2* | 2/2021 | Donavon | G16H 20/60 |
| 2005/0209178 A1 | 9/2005 | Pulst | |
| 2013/0195827 A1 | 8/2013 | Blum | |
| 2014/0310019 A1* | 10/2014 | Blander | G16H 40/67 705/2 |
| 2014/0343964 A1 | 11/2014 | Yoon | |
| 2016/0196389 A1* | 7/2016 | Moturu | G16H 50/20 705/2 |
| 2018/0122509 A1* | 5/2018 | Christiansson | G16H 10/60 |
| 2019/0251861 A1* | 8/2019 | Wolf | G16H 20/60 |
| 2019/0252058 A1* | 8/2019 | Wolf | G09B 19/0092 |
| 2019/0254331 A1 | 8/2019 | Astrup | |
| 2019/0290172 A1* | 9/2019 | Hadad | A61B 5/0022 |
| 2020/0005928 A1* | 1/2020 | Daniel | G16H 20/30 |
| 2020/0043596 A1* | 2/2020 | Koretoff | G16H 20/60 |
| 2020/0065681 A1* | 2/2020 | Wolf | G06N 20/00 |
| 2020/0066181 A1* | 2/2020 | Hadjigeorgiou | G09B 19/0092 |
| 2020/0211708 A1 | 7/2020 | Geronimo-Button | |
| 2020/0321113 A1* | 10/2020 | Neumann | G16H 50/00 |
| 2020/0321114 A1* | 10/2020 | Neumann | G16H 10/20 |
| 2020/0321116 A1* | 10/2020 | Neumann | G16H 20/10 |
| 2020/0321120 A1* | 10/2020 | Neumann | G06N 20/10 |
| 2020/0321122 A1* | 10/2020 | Neumann | G06N 20/20 |
| 2020/0321123 A1* | 10/2020 | Neumann | G16H 50/20 |
| 2020/0394565 A1* | 12/2020 | Neumann | G16H 50/20 |
| 2021/0005304 A1* | 1/2021 | Neumann | G16H 50/20 |
| 2021/0005317 A1* | 1/2021 | Neumann | G16H 50/20 |
| 2021/0327589 A1* | 10/2021 | Bradley | G01N 33/483 |

FOREIGN PATENT DOCUMENTS

| | | | |
|---|---|---|---|
| RU | 2691145 | 6/2019 | |
| WO | 0103700 A1 | 1/2001 | |
| WO | 2019074388 | 4/2019 | |
| WO | WO-2020069500 A1 * | 4/2020 | G06F 15/00 |

OTHER PUBLICATIONS

L. C. Rabelo, A. Jones and Y. Yih, "Development of a real-time learning scheduler using reinforcement learning concepts," Proceedings of 1994 9th IEEE International Symposium on Intelligent Control, Columbus, OH, USA, 1994, pp. 291-296, doi: 10.1109/ISIC.1994.367802. (Year: 1994).*

Title: Precision Nutrition: A Review of Personalized Nutritional Approaches for the Prevention and Management of Metabolic Syndrome; By: Toro Martin; Date: 2017.

http://dx.doi.org/10.3746/pnf.2015.20.1.1; Title: Obesity: Interactions of Genome and Nutrients Intake; By: Doo; Date: 2015.

Title: Insulin Receptor Substrate 1 Gene Variation Modifies Insulin Resistance Response to Weight-Loss Diets in a 2-Year Randomized Trial; By: 2011; By: Qibin.

Development of metabolic health assessment: Paving the way to disease prevention through personalized nutrition; By: Zivkovic; Date: Jun. 18, 1996.

* cited by examiner

500

108 148

- Adrenocorticoptropic hormone (ACTH)
- Antidiuretic hormone (ADH)
- Androstenedione
- Cortisol
- Aldosterone
- Renin
- Calcitonin
- Calcium
- Catecholamines
- Dehydroepiandrosterone (DHEA) sulfate
- Electrolytes
- Anion gap
- Estradiol
- Estriol
- Progesterone
- Follicle stimulating hormone (FSH)
- Growth hormone
- Human chorionic gonadotropin (hcg)
- Insulin like growth factor (IGF-1)
- Lutenizing hormone (LH)
- Plasma free metanephrines
- Urine metanephrines
- Prolactin
- Parathyroid hormone
- Sex hormone binding globulin (SHBG)
- Triiodothyronine (T3)
- Thyroxine (T4)
- Fine need aspiration
- Ultrasound
- Endoscopic ultrasound
- Computerized tomography (CT)
- Magnetic resonance imaging (MRI)
- Positron emission test (PET)
- Sestamibi scane

*FIG. 5*

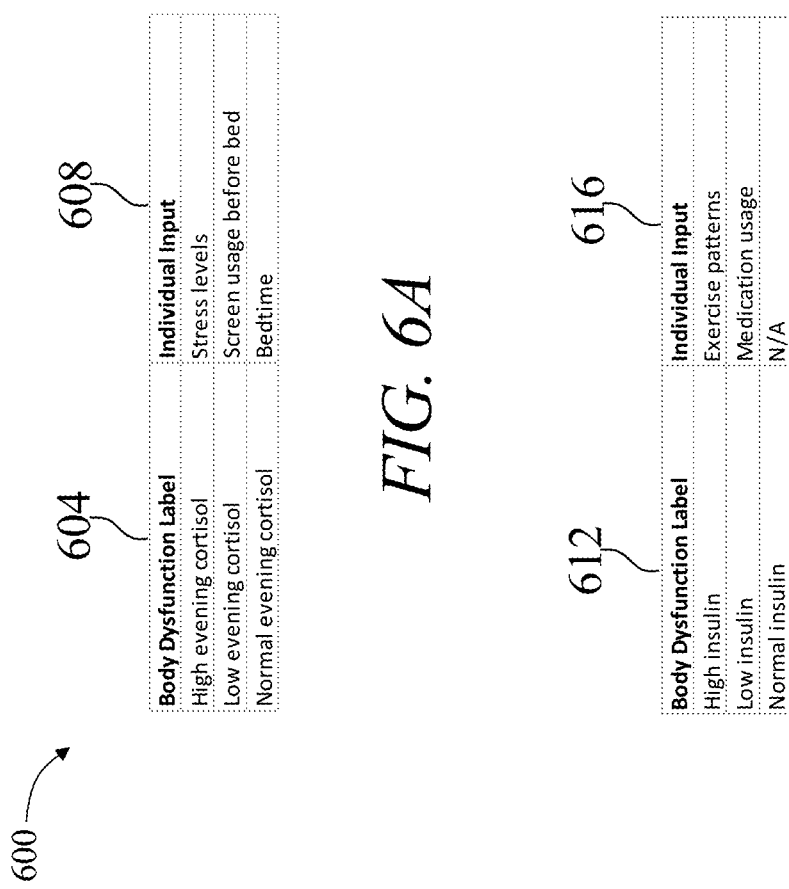

METHODS AND SYSTEMS FOR DIETARY COMMUNICATIONS USING INTELLIGENT SYSTEMS REGARDING ENDOCRINAL MEASUREMENTS

FIELD OF THE INVENTION

The present invention generally relates to the field of intelligent systems. In particular, the present invention is directed to methods and systems for dietary communications using intelligent systems regarding endocrinal measurements.

BACKGROUND

Endocrinal dysfunction can often go undetected. Minor abnormalities may not obtain necessary attention. This can further complicate one's ability to consume appropriate nutrition.

SUMMARY OF THE DISCLOSURE

In an aspect, a system for dietary communications using intelligent systems regarding endocrinal measurements, the system comprising a computing device designed and configured to obtain a first endocrinal measurement relating to a user; compare the first endocrinal measurement to an endocrinal system effect; generate a body dysfunction label for the first endocrinal measurement as a function of the endocrinal system effect; identify a dietary communication as a function of the body dysfunction label, the first endocrinal measurement, and a first machine learning process, the first machine learning process trained using a first training set relating endocrinal measurements and body dysfunction labels to dietary communications; and present the dietary communication.

In an aspect, a method of dietary communications using intelligent systems regarding endocrinal measurements, the method comprising obtaining, by a computing device, a first endocrinal measurement relating to a user; comparing, by the computing device, the first endocrinal measurement to an endocrinal system effect; generating, by the computing device, a body dysfunction label for the first endocrinal measurement as a function of the endocrinal system effect; identifying, by the computing device, a dietary communication as a function of the body dysfunction label, the first endocrinal measurement, and a first machine learning process, the first machine learning process trained using a first training set relating endocrinal measurements and body dysfunction labels to dietary communications; and presenting, by the computing device, the dietary communication.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 5 is a table illustrating an endocrinal measurement;

FIGS. 6A-B is a table illustrating a body dysfunction label and an individual input;

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for dietary communications using intelligent systems regarding endocrinal measurements. In an embodiment, a computing device obtains a first endocrinal measurement relating to a user. A computing device generates a body dysfunction label and identifies a dietary communication using a first machine learning process and a first training set.

Figure 1:
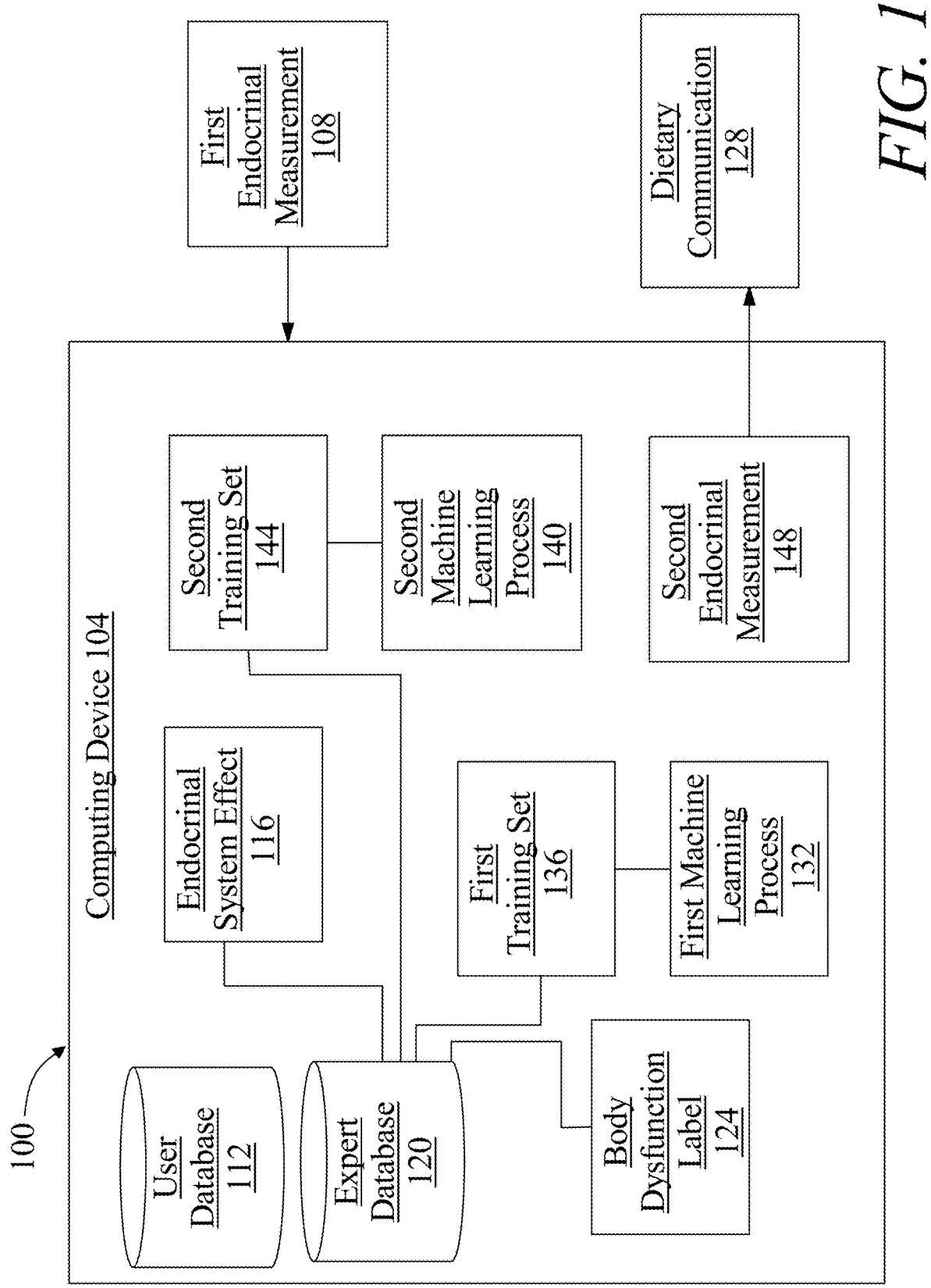
FIG. 1 is a block diagram illustrating an exemplary embodiment of a system for dietary communications using intelligent systems of endocrine measurements.

Referring now to the drawings, FIG. 1 illustrates an exemplary embodiment of a system 100 for dietary communications using intelligent systems regarding endocrinal measurements. System 100 includes a computing device 104. Computing device 104 may include any computing device as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus, or other relatively small geographic space), a telephone network, a data network associated with a telephone/voice provider (e.g., a mobile communications provider data and/or voice network), a direct connection between two computing devices, and any possibilities thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

With continued reference to FIG. 1. computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, computing device 104 is configured to obtain a first endocrinal measurement 108 relating to a user. An "endocrinal measurement," as used in this disclosure is a biological marker that may be a sign of a normal or abnormal endocrine process, an endocrinal condition, an endocrinal disease, and/or risk of developing a future endocrinal process, condition, and/or disease. An endocrinal measurement 108 may indicate the status and/or functioning of one or more endocrine glands including but not limited to the thyroid gland, the adrenal gland, the hypothalamus, exocrine glands, the pineal gland, the pituitary gland, the pancreas, the ovaries, the testes, the parathyroid gland, and the like. For instance and without limitation, an endocrinal measurement 108 may include but is not limited to one or more markers of the endocrine system such as adiponectin, adrenocorticotropic hormone (ACTH), antidiuretic hormone (ADH), androstenedione, cortisol, aldosterone, renin, calcitonin, calcium, catecholamine, dehydroepiandrosterone (DHEA) sulfate, electrolytes, anion gap, estradiol, estriol, progesterone, fasting glucose, follicle stimulating hormone (FSH), growth hormone, human chorionic gonadotropin (HCG), inulin like growth factor (IGF-1), insulin, luteinizing hormone (LH), plasma free metanephrines, prolactin, secretin, glucagon, calcitonin, brain derived neurotrophic factor, leptin, resistin, thrombopoietin, thyroglobulin antibody, thyroxine binding globulin, urine metanephrines, prolactin, parathyroid hormone, sex hormone binding globulin (SHBG), hemoglobin A1C, triiodothyronine (T3), thyroxine (T4), An endocrinal measurement 108 may be obtained from a physiological extraction including but not limited to a blood sample, a saliva sample, a urine sample, a stool sample, a hair sample, and the like. For instance, and without limitation, a first endocrinal measurement 108 such as a morning cortisol level may be obtained from a user's saliva sample. In yet another non-limiting example, a first endocrinal measurement 108 such as an estrone level may be obtained from a blood sample. An endocrinal measurement 108 may be obtained from a user response, such as information collected from a questionnaire, information collected from speaking with the user, user reports, and the like. For instance, and without limitation, a first endocrinal measurement 108 may include a user response to how frequently a user experiences symptom of hot flashes during a typical night's sleep. An endocrinal measurement 108 may be obtained from one or more tests and/or exams, including for example fine needle aspiration, sestamibi scan, ultrasound, endoscopic ultrasound, computerized tomography (CT), magnetic resonance imaging (MM), positron emission test (PET), radioactive iodine scan, octreoscan, meta iodo benzo guanidine (MIBG) scan, venous sampling, radioactive iodine uptake test, and the like.

With continued reference to FIG. 1, first endocrinal measurement 108 may identify a current endocrine disorder. A "current endocrine disorder," as used in this disclosure, is a condition, syndrome, disease, and/or process relating to the endocrine system that the user is presently diagnosed with. For instance and without limitation, a current endocrine disorder may include for example adrenal insufficiency, acromegaly, Cushing's disease, gigantism, hyperthyroidism, hypothyroidism, hypopituitarism, multiple endocrine neoplasia I (MEN I), multiple endocrine neoplasia I (MEN II), polycystic ovary syndrome (PCOS), precocious puberty, Type 1 diabetes mellitus, Type 2 diabetes mellitus, osteoporosis, thyroid cancer, Addison's disease, Cushing's syndrome, graves' disease, hash moto's thyroiditis, prediabetes, growth hormone insufficiency, goiter, gestational diabetes, diabetes insipidus, obesity, thyroiditis, thyroid nodule, turner syndrome, and the like. First endocrinal measurement 108 may identify a probable endocrinal disorder. A "probable endocrinal disorder," as used in this disclosure, is an endocrinal disorder that a user is presently not diagnosed with but may be at risk of developing in the future. For example, a user with a repeatedly elevated fasting glucose level may be indicated as containing a probable endocrinal disorder such as Type 2 diabetes mellitus. In yet another non-limiting example, a user with a genetic pattern indicating mutations of genes involved in steroidogenesis such as CYP11a, CYP21, CYP17, and CYP19 may be at risk of developing an endocrinal disorder such as polycystic ovarian syndrome (PCOS).

With continued reference to FIG. 1, information relating to an endocrinal measurement may be contained within user database 112. User database 112 may be implemented, without limitation, as a relational database, a key-value retrieval datastore such as a NOSQL database, or any other format or structure for use as a datastore that a person skilled in the art would recognize as suitable upon review of the entirety of this disclosure. User database 112 may contain one or more entries containing information relating to a user.

With continued reference to FIG. 1, computing device 104 is configured to compare first endocrinal measurement 108 to an endocrinal system effect 116. An "endocrinal system effect," as used in this disclosure, is a reference range indicating normal ranges and/or expected values for a first endocrinal measurement 108. For instance, and without limitation, a hemoglobin A1C value less than 5.7% may be considered an endocrinal system effect, or a reference range indicating a value of an A1C measurement expected in a user who does not have diabetes mellites. Comparing may include evaluating a first endocrinal measurement 108 in relation to an endocrinal system effect 116. For instance and without limitation, a first endocrinal measurement 108 such as a morning salivary cortisol level of 7.0 ng/ml may be compared to an endocrinal system effect 116 which indicates that the standard reference range for a morning salivary cortisol level is between 3.7-9.5 ng/ml. Computing device 104 may select an endocrine system effect 116 as a function of a user attribute. A "user attribute," as used in this disclosure, is a quality and/or feature that may be pertinent to the selection of an endocrine system effect 116. A user attribute may include information about the user such as the user's age or sex. A user attribute may include information about a particular life stage and/or event a user may be at in the user's life. For instance and without limitation, a user attribute may identify if a user is an adolescent, a young adult, pre-menopausal, andropause, and the like. Computing device 104 may select an endocrinal system effect 116 utilizing a user attribute. For instance and without limitation, a user attribute that indicates a user is a 26-year-old female may be utilized to select an endocrinal system effect 116 for a first endocrinal measurement 108 that contains a reference range intended for premenopausal women, while a user attribute that indicates a user has diagnosed Type 2 Diabetes Mellitus may be utilized to choose a reference range that is intended for diabetics. Information pertaining to an endocrinal system effect may be obtained from top medical experts having certain board qualifications and/or certifications, scientific articles, journals, literature, and the like. Such information may be stored and contained within expert database 120. Expert database 120 may be implemented as any data structure suitable for use as user database 112 as described above in more detail.

With continued reference to FIG. 1, computing device 104 is configured to generate a body dysfunction label 124. A "body dysfunction label," as used in this disclosure, is an indicator of the current state of a user's endocrine system. A body dysfunction label 124 may indicate if a first endocrinal measurement 108 is within normal limits, and/or outside normal limits. For instance, and without limitation, a body dysfunction label 124 may indicate that a first endocrinal measurement 108 is within normal limits for a user with a diagnosed endocrinal disorder such as gestational diabetes but is outside normal limits for a user without a diagnosed endocrinal disorder. In yet another non-limiting example, a body dysfunction label 124 may indicate that a first endocrinal measurement 108 is outside normal limits for a user without a diagnosed endocrinal disorder. Information pertaining to a body dysfunction label 124 may be stored and contained within expert database 120. In an embodiment, a body dysfunction label 124 may indicate how far astray a first endocrinal measurement 108 may be from an endocrinal system effect 116. For instance, and without limitation, a body dysfunction label 124 may specify that a first endocrinal measurement 108 is barely outside normal limits such as if a first endocrinal measurement 108 for a thyroid stimulating hormone (TSH) has a value of 0.4 miU/L and the standard reference range for a TSH is between 0.5-5.0 miU/L. In yet another non-limiting example, a body dysfunction label 124 may specify that a first endocrinal measurement 108 is grossly outside normal limits such as if a first endocrinal measurement for a fasting glucose level is 304 mg/dl and the standard reference range for a fasting glucose level is between 60-99 mg/dl.

With continued reference to FIG. 1, computing device 104 is configured to identify a dietary communication 128 as a function of body dysfunction label 124, first endocrinal measurement 108, and a first machine learning process 132. A "dietary communication," as used in this disclosure, is personalized nutritional information. Personalized nutritional information may include information describing restricted and/or allowed nutrients. Restricted nutrients may include any ingredient that may contain a limitation. An "ingredient," as used in this disclosure, is any food and/or substance intended for consumption by a human being. A limitation may specify a maximum quantity of an ingredient that is recommended to be consumed by a user. For example, a limitation may specify that a user is to consume no more than 2 kiwifruit per day. A limitation may specify a minimum quantity of an ingredient that is recommended to be consumed by a user. For example, a limitation may specify that a user is to consume at least 5 grams of beta glucan per day. A limitation may specify an optimal time of day when one or more ingredients is recommended to be consumed. For example, a limitation may specify that a user is recommended to consume an ingredient such as dark chocolate at 3 pm every day. A limitation may specify a quantity of an ingredient that a user is recommended to consume. For example, a limitation may specify that a user is to consume half a cup of rainier cherries half an hour before bedtime. A limitation may specify an ingredient that a user is recommended to avoid completely and/or is only to consume in limited quantities. For example, a limitation may specify that a user is to avoid consuming all eggs and all egg containing products for a minimum of at least 4 weeks. In yet another non-limiting example, a limitation may specify that a user is to consume no more than six grams of added sugar per day. A limitation may specify one or more ingredients that may be recommended to be consumed together in combination. For example, a limitation may suggest that a first ingredient such as tomato may have optimal nutrients absorbed when combined together with a second ingredient such as broccoli. Information pertaining to a limitation may be contained within expert database 120. An "allowed nutrient," as used in this disclosure, is any ingredient that does not contain a limitation. For instance, and without limitation, an allowed nutrient may include a nutrient such as red bell peppers, which a user may be free to consume in any quantity the user may desire.

With continued reference to FIG. 1, a "machine learning process," as used in this disclosure, is a process that automatically uses training data to generate an algorithm that will be performed by computing device 104 to produce outputs given data provided as inputs; this is in contrast to a non-machine learning software program where the commands to be executed are determined in advance by a user and written in a programming language. First machine learning process 132 may be trained using a first training set 136. A "training set," as used in this disclosure is data containing correlations that a machine learning process may use to model relationships between two or more categories of data elements. For instance, and without limitation, first training set 136 may include a plurality of data entries, relating endocrinal measurements and body dysfunction labels to dietary communications. First training set 136 may be obtained from one or more sources, including for example expert input, public forums, publications, and the like. Information pertaining to first training set 136 may be contained within expert database 120.

With continued reference to FIG. 1, computing device 104 may be configured to choose an individual input as a function of a body dysfunction label 124. An "individual input," as used in this disclosure, is additional information requested to be known about a user. Information pertaining to an individual input may be contained within user database 112. Additional information may include information pertaining to a user's personal life including demographic information such as if the user is married or lives alone. Additional information may include information pertaining to a user's fitness patterns, such as any physical activity the user engages in, how often the user engages in physical activity, and/or types of physical activity the user engages in such as cardiovascular training or weight training. Additional information may include information pertaining to a user's health habits, including any prescription, non-prescription, supplements, over the counter medication, herbal remedies, nutraceuticals, and the like that the user consumes. Additional information may include information pertaining to a user's stress management practice, such as if the user engages in yoga, tai-chi, meditation, and the like. Additional information may include information pertaining to a user's overall financial wellness and spending habits. Additional information may include any information describing any co-morbidities that the user may suffer from. A "co-morbidity," as used in this disclosure, any simultaneous medical condition and/or disease that a user may suffer from. For instance, and without limitation, a co-morbidity may indicate that a user suffers from a medical condition such as rheumatoid arthritis. In an embodiment, a co-morbidity may also specify if the simultaneous medical condition and/or disease is acute or chronic, and/or may also specify any treatments the user may be taking associated with the co-morbidity. In an embodiment, computing device 104 may choose an individual input as a function of a body dysfunction label 124. For instance, and without limitation, a body dysfunction label 124 that indicates a first endocrinal measurement 108 for a Hemoglobin A1C level that is grossly outside normal limits and alarmingly high thus indicating a high likelihood of blood sugar dysfunction, may prompt computing device 104 to choose an individual input such as a user's fitness habits. In yet another non-limiting example, a body dysfunction label 124 that indicates a first endocrinal measurement 108 for a morning salivary cortisol level that is slightly low may prompt computing device 104 to choose an individual input such as a user's sleep habits to collect more information about what time on average a user goes to bed, and what time on average the user wakes up in the morning. Computing device 104 may receive an entry relating to an individual input from a user. This may be performed utilizing any network methodology as described herein. Computing device 104 may identify a dietary communication 128 utilizing an individual input. In an embodiment, this may include utilizing an individual input as an input to first machine learning process 132.

With continued reference to FIG. 1, computing device 104 may receive an individual input from a wearable device. A "wearable device," as used in this disclosure, is an electronic device that may detect, analyze, and/or transmit information concerning a user. A wearable device may make contact with and/or touch one or more body parts of a user, including but not limited to the fingers, palm, wrists, chest, forearms, ears, eyes, ear canal, forehead, temple, back, foot, ankle, and the like. In an embodiment, a wearable device 104 may not make contact and/or touch one or more body parts of a user, but rather may be in the vicinity and/or located adjacent to a user, such as a computer and/or mobile phone, as described below in more detail. A wearable device may be worn as an accessory, embedded in clothing worn by a user, implanted on a user's body, and/or tattooed onto a user's skin. For instance, and without limitation, a wearable device may include a smartwatch, a fitness tracker, a sports watch, a head-mounted display, a virtual reality headset, smart glasses, hearables, smart jewelry, smart clothing, hearing aids, and the like. A wearable device may include any electrical equipment controlled by a central processing unit (CPU) such as but not limited to a laptop computer, a desktop computer, a smartphone, a mobile device, a computerized medical device, a tablet, and the like.

With continued reference to FIG. 1, computing device 104 is configured to generate a second machine learning process 140. Second machine learning process may include any machine learning process suitable for use as first machine learning process 132 as described above in more detail. Second machine learning process 140 may be trained using a second training set 144. Second training set 144 may include any training set as described above in more detail. Second training set 144 may relate endocrinal system effects to body dysfunction labels. Second training set 144 and second machine learning process 140 may be used to generate body dysfunction label 124. Second training set 144 may be obtained from expert input, public disclosures, journal articles, printed publications, previous user entries, previous iterations of first and/or second machine learning process and the like.

With continued reference to FIG. 1, computing device 104 is configured to obtain a second endocrinal measurement 148 related to a first endocrinal measurement 108. A second endocrinal measurement 148 may include any measurement suitable for use as first endocrinal measurement 108 as described above in more detail. A second endocrinal measurement 148 may relate to a first endocrinal measurement 108 such as when the first endocrinal measurement 108 may be commonly measured together in combination with the second endocrinal measurement 148. For instance, and without limitation, a first endocrinal measurement 108 such as a fasting blood glucose level may be commonly measured together in combination with a second endocrinal measurement 108 such as a Hemoglobin A1c. A second endocrinal measurement 148 may relate to a first endocrinal measurement 108 such as when the first endocrinal measurement 108 may require follow up with a second endocrinal measurement 148. For instance, and without limitation, a first endocrinal measurement 108 such as an estradiol measurement may warrant follow up with a second endocrinal measurement 148 such as a progesterone measurement. In yet another non-limiting example, a first endocrinal measurement 108 such as an insulin level may warrant follow up with a second endocrinal measurement 148 such as a subsequent insulin level at a later date in time. Information pertaining to first endocrinal measurements 108 that may relate to second endocrinal measurements 148 may be stored and contained within expert database 120.

With continued reference to FIG. 1, computing device 104 is configured to present a dietary communication 128. Presenting may include displaying a dietary communication 128 on computing device 104. Presenting may include transmitting a dietary communication 128 to a wearable device and/or remote device such as a cell phone, tablet, and/or computer operated by a user. This may be performed utilizing any network methodology as described herein.

Figure 2:
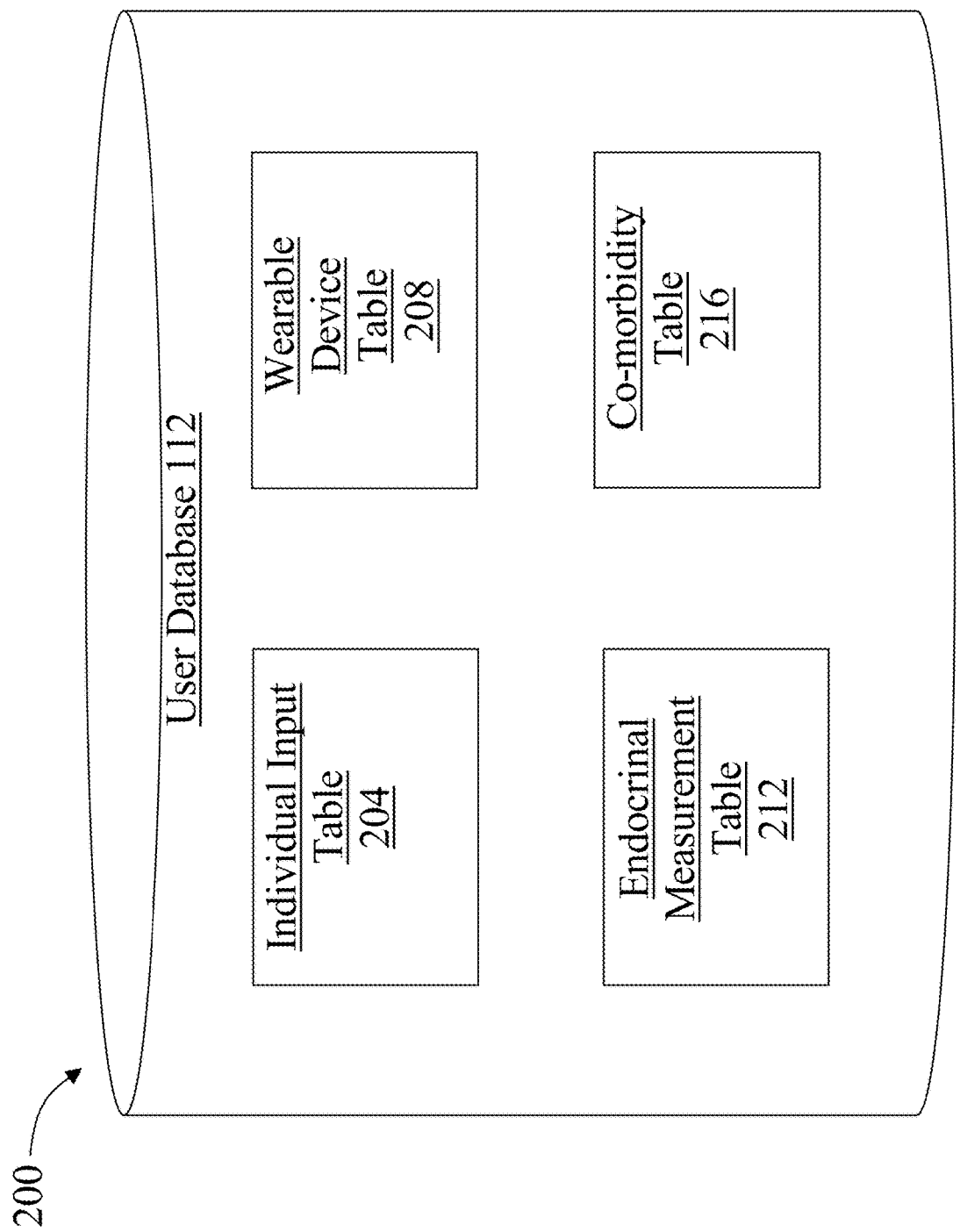
FIG. 2 is a block diagram illustrating a user database.

Referring now to FIG. 2, an exemplary embodiment 200 of user database 112 is illustrated. User database 112 may be implemented as any data structure suitable for use as described above in more detail in reference to FIG. 1. One or more tables contained within user database 112 may include individual input table 204; individual input table 204 may include any entries from a user describing an individual input. For instance, and without limitation, individual input table 204 may contain a user's sleep patterns collected from a wearable device worn by the user. One or more tables contained within user database 112 may include wearable device table 208; wearable device table 208 may include information from a wearable device of the user. For instance, and without limitation, wearable device table 208 may include data collected by a fitness tracker worn by the user. One or more tables contained within user database 112 may include endocrinal measurement table 212; endocrinal measurement table 212 may contain one or more endocrinal measurements relating to a user. For instance, and without limitation, endocrinal measurement table 212 may contain an entry with the results and findings from a pelvic ultrasound. One or more tables contained within user database 112 may include co-morbidity table 216; co-morbidity table 216 may include any information describing any co-morbidities and/or previous diagnoses a user may have been diagnosed with. For instance, and without limitation, co-morbidity table 216 may include an entry describing a co-morbidity of a user, such as hypertension.

Figure 3:
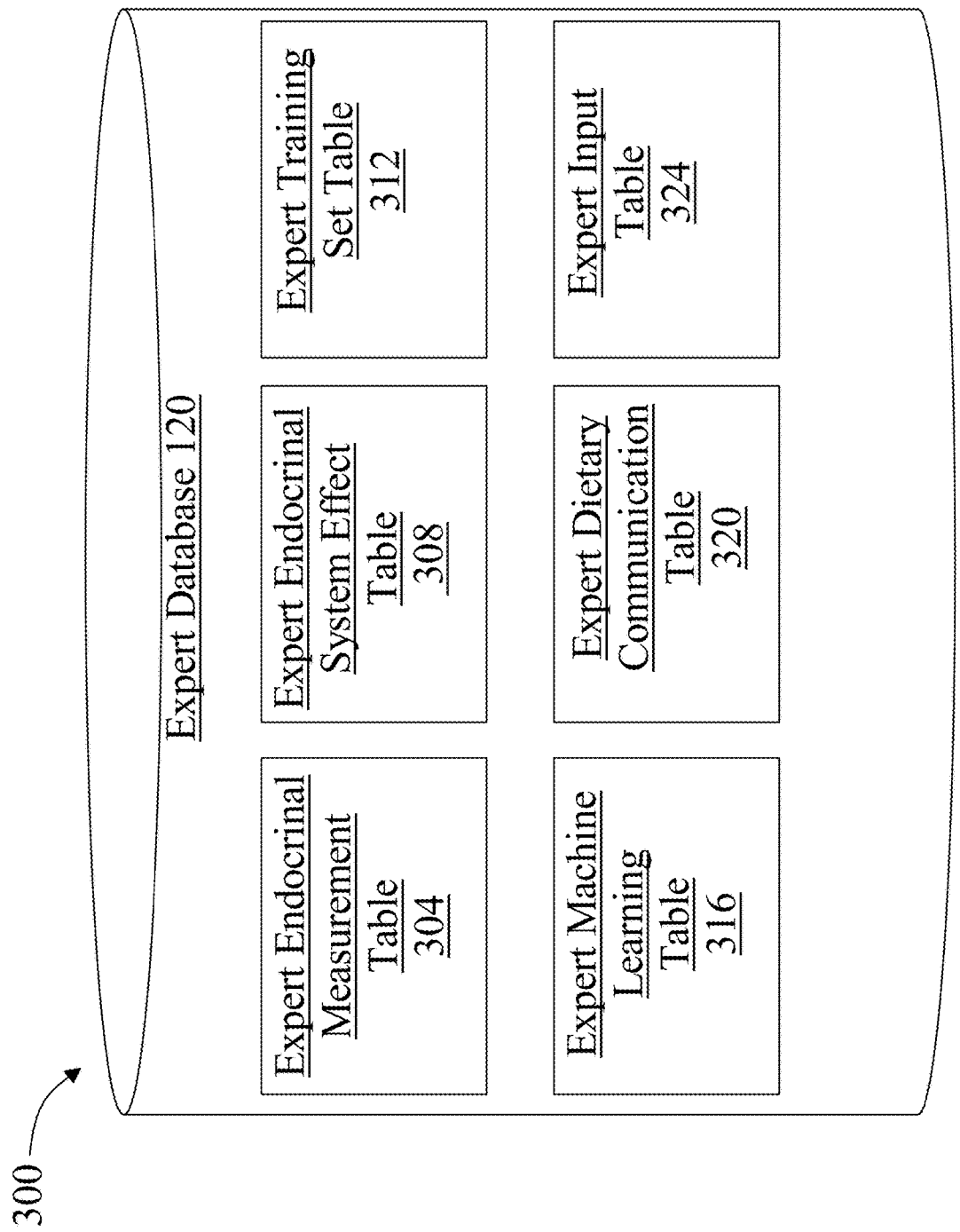
FIG. 3 is a block diagram of an expert database.

Referring now to FIG. 3, an exemplary embodiment 300 of expert database 120 is illustrated. Expert database 120 may be implemented as any data structure suitable for use as user database 112 as described above in more detail in reference to FIG. 12. One or more tables contained within expert database 120 may include expert endocrinal measurement table 304; expert endocrinal measurement table 304 may include information describing expert entries relating to endocrinal measurements. One or more tables contained within expert database 120 may include expert endocrinal system effect table 308; expert endocrinal system effect table 308 may include information describing expert entries relating to endocrinal system effects. One or more tables contained within expert database 120 may include expert training data table 312; expert training set table 312 may include expert entries relating to training sets. One or more tables contained within expert database 120 may include expert machine learning table 316; expert machine learning table 316 include expert entries relating to machine learning processes. One or more entries contained within expert database 120 may include expert dietary communication table 320; expert dietary communication table 320 may include expert entries relating to dietary communications. One or more tables contained within expert database 120 may include expert input table 324; expert input table 324 may include expert entries relating to individual inputs.

Figure 4:
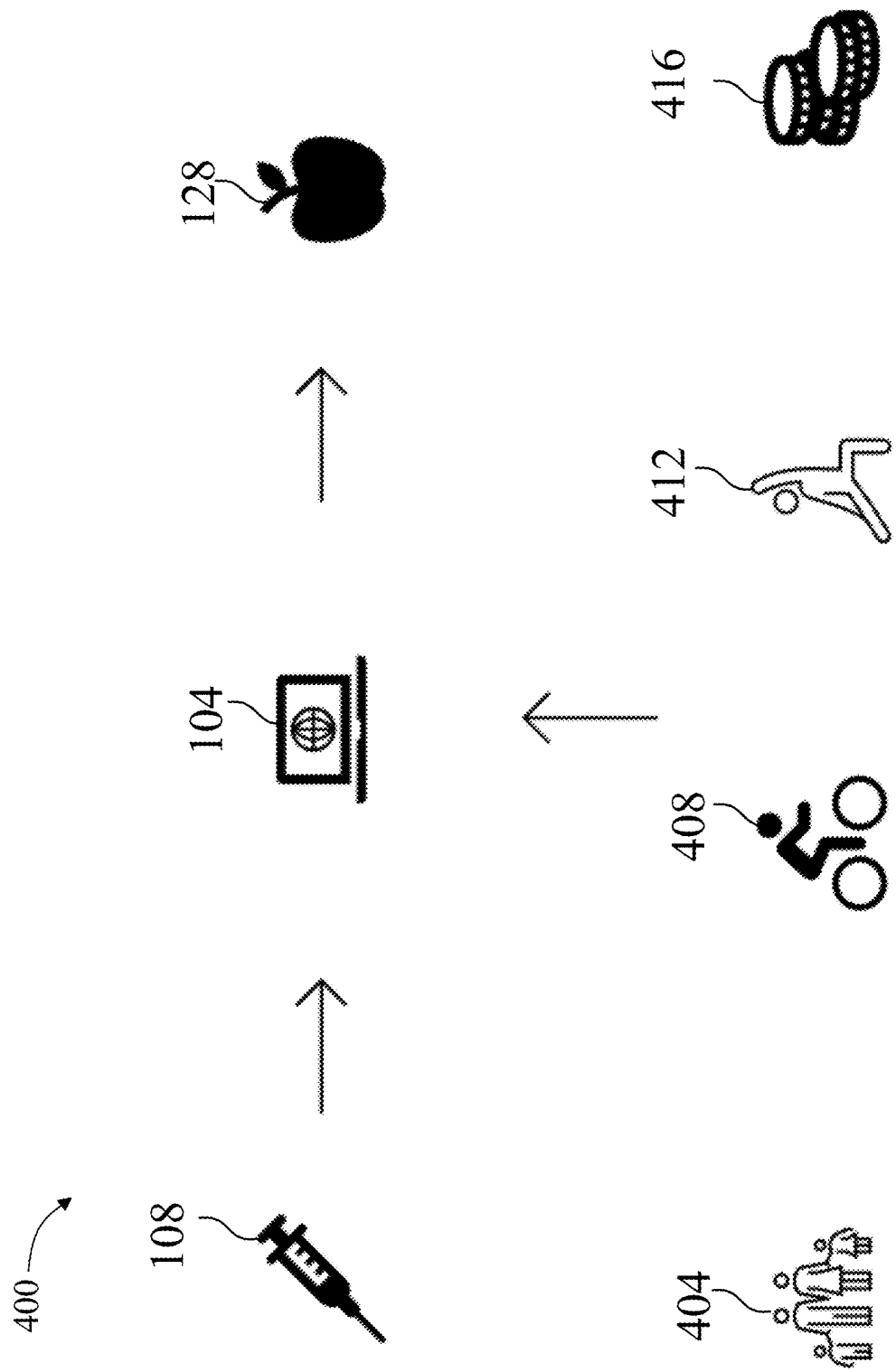
FIG. 4 is a diagrammatic representation of an individual input.

Referring now to FIG. 4, an exemplary embodiment 400 of individual inputs is illustrated. In an embodiment, a first endocrinal measurement 108 is utilized by computing device 104, in combination with first machine learning process 132 to output a dietary communication 128. In an embodiment, an individual input may be chosen as a function of a body dysfunction label 124, to obtain more information relating to a user's personal life, wellness, fitness habits and the like which may inform generation of a dietary communication 128. In an embodiment, an individual input may include information pertaining to a user's family and home life 404. This may include information such as how many persons the user lives with, if the user has any children, how many pets the user has, the user's marital status, and the like. In an embodiment, an individual input may include information pertaining to a user's fitness patterns 408. This may include information describing the types of exercise the user enjoys, how often the user engages in exercise, duration of exercise, and the like. In an embodiment, an individual input may include information pertaining to a user's stress management practice 412. This may include information describing any stress management techniques that a user engages in, including for example, any yoga, meditation, tai-chi, breath focus, guided imagery, repetitive prayer, progressive muscle relaxation and the like. In an embodiment, an individual input may include information pertaining to a user's financial wellbeing 416. This may include information describing any information such as a user's control over monthly finances, being on track to meet financial goals, attaining financial freedom, and the like.

Referring now to FIG. 5, an exemplary embodiment 500 regarding endocrinal measurements is illustrated. In an embodiment, first endocrinal measurement 108 and/or second endocrinal measurement 148 may include but are not limited to one or more of the measurements listed, as described above in more detail in reference to FIG. 1.

Referring now to FIGS. 6A-6B, an exemplary embodiment 600 of body dysfunction labels and individual inputs is illustrated. Referring first to FIG. 6A, in an embodiment, a body dysfunction label 604 may be mapped to one or more individual inputs 608. For instance, and without limitation, a body dysfunction label 604 including for example a first endocrinal measurement 108 and/or a second endocrinal measurement 148 such as a high evening cortisol level may be mapped to an individual input 608 such as stress levels. In yet another non-limiting example, a body dysfunction label 604 such as low evening cortisol may be mapped to an individual input 608 such as screen usage before bed. In an embodiment, body dysfunction labels 604 may be categorized based on one or more endocrinal measurements. Referring now to FIG. 6B, in an embodiment, a body dysfunction label 612 may include a measurement such as a high insulin level which may be mapped to an individual input 616 such as learning about a user's exercise patterns. In yet another non-limiting example, a body dysfunction label 612 may include a measurement such as a low insulin level which may be mapped to an individual input 616 such as medication usage.

Figure 7:
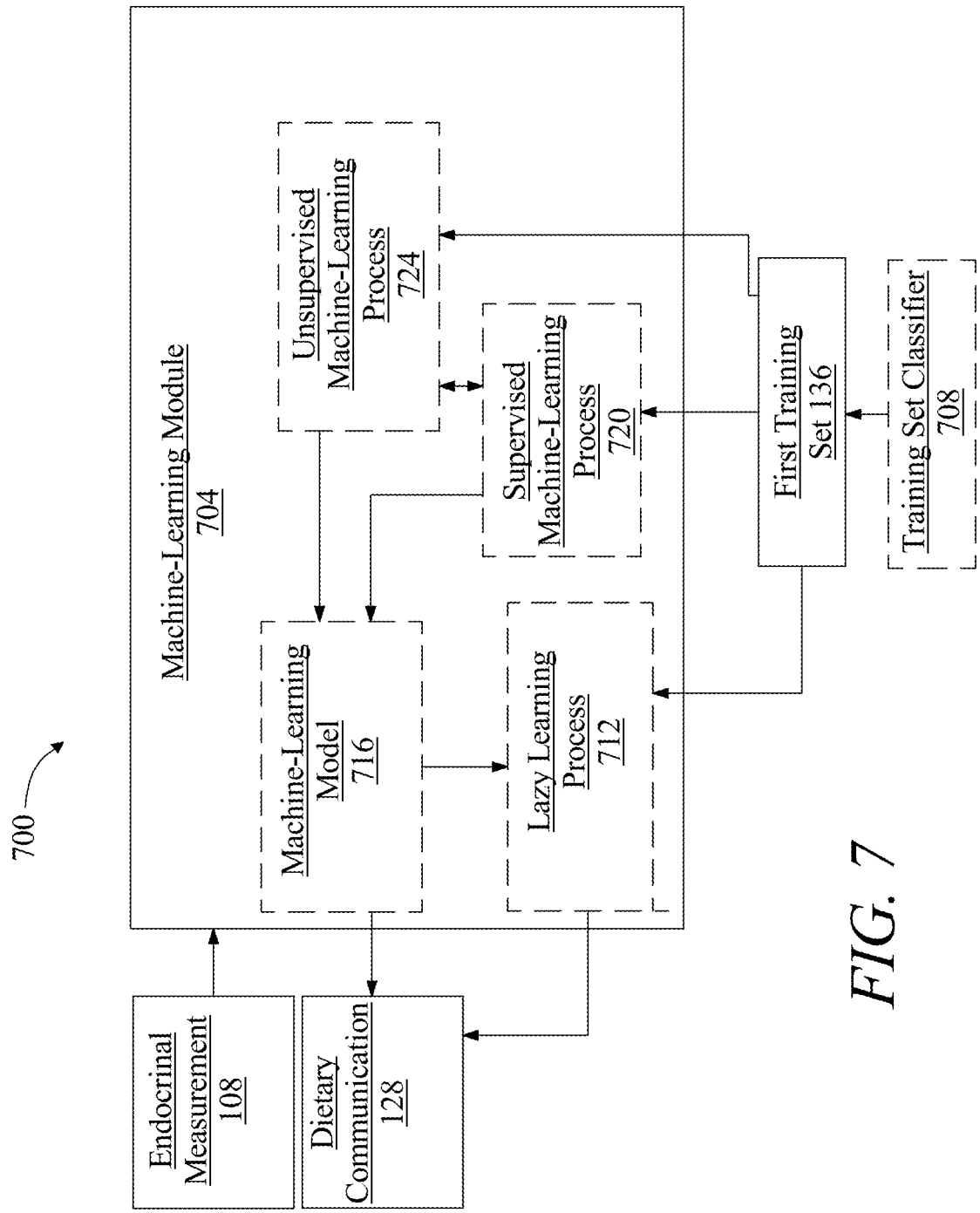
FIG. 7 is a block diagram illustrating a machine learning module.

Referring now to FIG. 7, an exemplary embodiment 700 of a machine-learning module 704 that may perform one or more machine-learning processes as described in this disclosure is illustrated. Machine-learning module may perform determinations, classification, and/or analysis steps, methods, processes, or the like as described in this disclosure using machine learning processes. A machine learning process may include for example, first machine learning process 132 and/or second machine learning process 140. A machine learning process may be trained using first training set 136 and/or second training set 144 as described above in more detail.

With continued reference to FIG. 7, first training set 136 may include a plurality of data entries, each entry representing a set of data elements that were recorded, received, and/or generated together; data elements may be correlated by shared existence in a given data entry, by proximity in a given data entry, or the like. Multiple data entries in first training set 136 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in first training set 136 according to various correlations; correlations may indicate causative and/or predictive links between categories of data elements, which may be modeled as relationships such as mathematical relationships by machine-learning processes as described in further detail below. First training set 136 may be formatted and/or organized by categories of data elements, for instance by associating data elements with one or more descriptors corresponding to categories of data elements. As a non-limiting example, first training set 136 may include data entered in standardized forms by persons or processes, such that entry of a given data element in a given field in a form may be mapped to one or more descriptors of categories. Elements in first training set 136 may be linked to descriptors of categories by tags, tokens, or other data elements; for instance, and without limitation, first training set 136 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data. As a non-limiting illustrative example, first training set 136 may contain endocrinal measurements and body dysfunction labels as inputs, and dietary communications as outputs. In yet another non-limiting example, second training set 144 may contain endocrinal system effects as an input, and body dysfunction labels as outputs.

Alternatively, or additionally, and continuing to refer to FIG. 7, first training set 136 may include one or more elements that are not categorized; that is, first training set 136 may not be formatted or contain descriptors for some elements of data. Machine-learning algorithms and/or other processes may sort first training set 136 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same first training set 136 to be made applicable for two or more distinct machine-learning algorithms as described in further detail below. First training set 136 used by machine-learning module 704 may correlate any input data as described in this disclosure to any output data as described in this disclosure.

Further referring to FIG. 7, training data may be filtered, sorted, and/or selected using one or more supervised and/or unsupervised machine-learning processes and/or models as described in further detail below; such models may include without limitation a training set classifier 708. Training set classifier 708 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 704 may generate a classifier using a classification algorithm, defined as a process whereby a computing device and/or any module and/or component operating thereon derives a classifier from first training set 136. Classification may be performed using, without limitation, linear classifiers such as without limitation logistic regression and/or naive Bayes classifiers, nearest neighbor classifiers such as k-nearest neighbors' classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training set classifier 708 may classify elements of training data to specific endocrinal measurements and/or body dysfunction labels for example.

Still referring to FIG. 7, machine-learning module 704 may be configured to perform a lazy-learning process 712 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of first training set 136. Heuristic may include selecting some number of highest-ranking associations and/or first training set 136 elements. Lazy learning may implement any suitable lazy learning algorithm, including without limitation a K-nearest neighbors' algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively, or additionally, and with continued reference to FIG. 7, machine-learning processes as described in this disclosure may be used to generate machine-learning models 716. A "machine-learning model," as used in this disclosure, is a mathematical and/or algorithmic representation of a relationship between inputs and outputs, as generated using any machine-learning process including without limitation any process as described above and stored in memory; an input is submitted to a machine-learning model 716 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 716 may be generated by creating an artificial neural network, such as a convolutional neural network comprising an input layer of nodes, one or more intermediate layers, and an output layer of nodes. Connections between nodes may be created via the process of "training" the network, in which elements from a first training set 136 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 7, machine-learning algorithms may include at least a supervised machine-learning process 720. At least a supervised machine-learning process 720, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include inputs as described above as inputs, outputs as described above as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 704. Persons skilled in the art, upon reviewing the entirety of this disclosure, will be aware of various possible variations of at least a supervised machine-learning process 720 that may be used to determine relation between inputs and outputs. Supervised machine-learning processes may include classification algorithms as defined above.

Further referring to FIG. 7, machine learning processes may include at least an unsupervised machine-learning processes 724. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 7, machine-learning module 700 may be designed and configured to create a machine-learning model 724 using techniques for development of linear regression models. Linear regression models may include ordinary least squares regression, which aims to minimize the square of the difference between predicted outcomes and actual outcomes according to an appropriate norm for measuring such a difference (e.g., a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g., a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 7, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors' algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Figure 8:
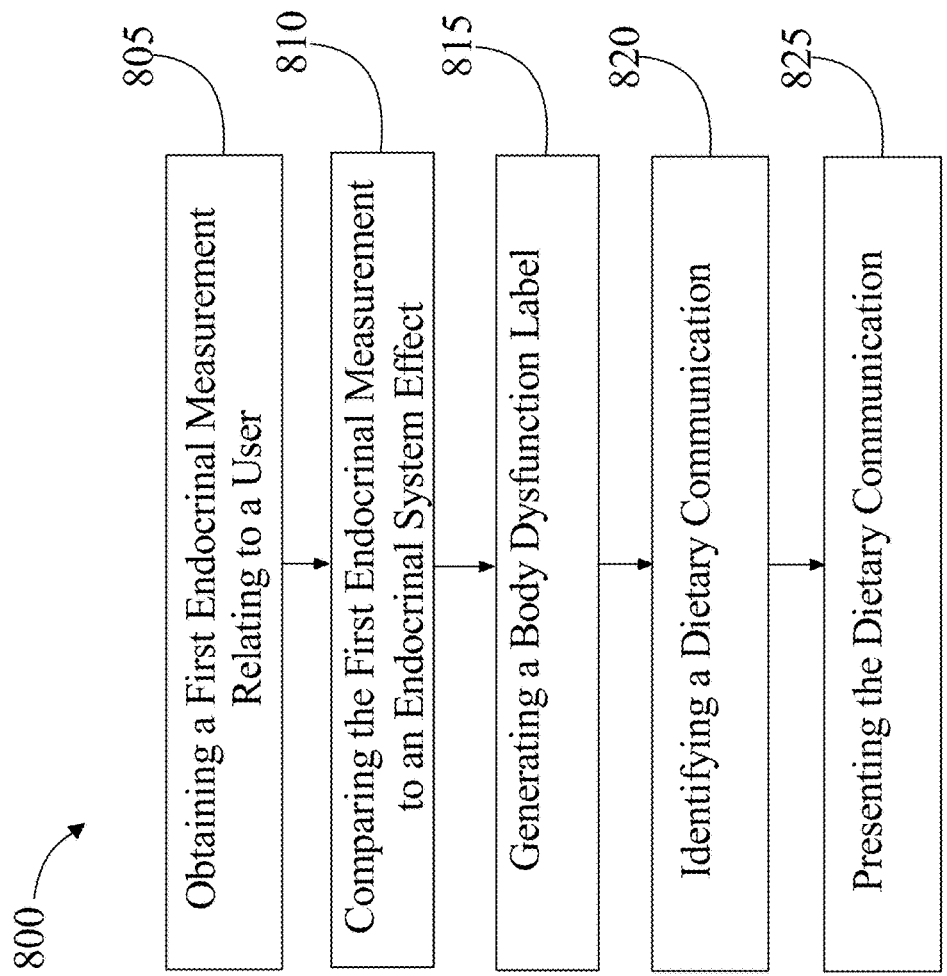
FIG. 8 is a process flow diagram illustrating an exemplary embodiment of a method of dietary communications using intelligent systems of endocrine measurements.

Referring now to FIG. 8, an exemplary embodiment 800 of a method of dietary communication using intelligent systems regarding endocrine measurements is illustrated. At step 805, computing device 104 obtains a first endocrinal measurement 108. First endocrinal measurement 108 includes any of the endocrine measurements as described above in more detail in reference to FIGS. 1-7. For instance, and without limitation, an endocrinal measurement 108 may include results from a blood sample analyzed for testosterone levels. In yet another non-limiting example, an endocrinal measurement 108 may include findings from a thyroid ultrasound. In an embodiment, a first endocrinal measurement 108 may identify a current endocrinal disorder. For example, a first endocrinal measurement 108 may specify that a user is currently diagnosed as having an endocrine disorder such as hyperthyroidism. In an embodiment, a first endocrinal measurement 108 may identify a probable endocrinal disorder. For example, a first endocrinal measurement 108 may specify that a user with subclinical hypothyroidism may be at risk of later developing hypothyroidism. In yet another non-limiting example, a first endocrinal measurement 108 may specify that a user with a variant of the HLA-DQA1 gene may be at risk of developing Type 1 Diabetes Mellites. Information pertaining to a first endocrinal measurement 108 may be stored within user database 112.

With continued reference to FIG. 8, at step 810, computing device 104 compares a first endocrinal measurement 108 to an endocrinal system effect 116. An endocrinal system effect 116 includes any of the endocrinal system effects as described above in more detail in reference to FIG. 1. In an embodiment, comparing may include evaluating by computing device 104 how a first endocrinal measurement 108 performs in relation to an endocrinal system effect 116. For instance, and without limitation, a first endocrinal measurement 108 such as a salivary progesterone level of 52 pg/ml may be evaluated in relation to an endocrinal system effect 116 having a reference range of salivary progesterone levels ranging anywhere from 75-250 pg/ml. Information pertaining to an endocrinal system effect 116 may be stored within expert database 120.

With continued reference to FIG. 8, at step 815, computing device 104 generates a body dysfunction label 124 for first endocrinal measurement 108 as a function of an endocrinal system effect 116. A body dysfunction label 124 includes any of the body dysfunction labels 124 as described above in more detail in reference to FIGS. 1-7. A body dysfunction label 124 may indicate the current state of a user's endocrine system. For example, a body dysfunction label 124 may indicate if a first endocrinal measurement 108 is within expected limits and/or outside expected limits. In yet another non-limiting example, a body dysfunction label 124 may indicate one or more endocrinal disorders and/or diseases that a user may be at risk of contracting. In an embodiment, computing device 104 may generate body dysfunction label 124 utilizing a second machine learning process 140. Computing device 104 may generate second machine learning process 140 using any of the methodologies as described above in more detail in reference to FIG. 7. Second machine learning process 140 may be trained using second training set 144 relating endocrinal system effects to body dysfunction labels. Computing device 104 may generate body dysfunction label as a function of generating second machine learning process 140.

With continued reference to FIG. 8, at step 820, computing device 104 identifies a dietary communication 128 as a function of a body dysfunction label 124, a first endocrinal measurement 108. Identifying includes training a first machine learning process 132 using first training set 136 relating endocrinal measurements and body dysfunction labels to dietary communications and identifying the dietary communication as a function of the body dysfunction label, the first endocrinal measurement, and the first machine learning process 132. First machine learning process 132 may be implemented using any methodology as described above in more detail in reference to FIG. 7. First machine learning process may be trained using a first training set 136 relating endocrinal measurements and body dysfunction labels 124 to dietary communications 128. A dietary communication 128 includes any of the dietary communications as described above in more detail in reference to FIG. 1. A dietary communication 128 may contain personalized nutritional information. For instance, and without limitation, a dietary communication 128 may contain a meal plan with recommended meals and/or ingredient combinations that may be recommended to treat, prevent, and/or reverse any endocrinal dysfunction of a user. A dietary communication 128 may identify restricted nutrients and allowed nutrients, as described above in more detail in reference to FIG. 1. For instance, and without limitation, a dietary communication 128 may identify restricted nutrients such as tomatoes which are to be consumed in quantities of no more than half a cup per day, as well as allowed nutrients such as carrots which a user can consume in any quantity and/or with any frequency that the user desires. Computing device 104 may generate dietary communication 128 using additional information about a user. For example, computing device 104 may choose an individual input as a function of a body dysfunction label. This may be performed utilizing any methodologies as described above in more detail. For example, a body dysfunction label 124 which indicates that a user has impaired glucose tolerance may be utilized by computing device 104 to choose an individual input to ascertain information such as what times of the day the user consumes meals and what size meals the user is consuming. Computing device 104 may receive an entry relating to an individual input from a user. This may be performed utilizing any network methodology as described herein. Computing device 104 may identify a dietary communication 128 as a function of an individual input. Information pertaining to an entry relating to an individual input may be stored within user database 112. In an embodiment, information pertaining to an individual input may be received from a wearable device. Wearable device includes any of the wearable devices as described above in more detail in reference to FIGS. 1-7. In an embodiment, an individual input may relate to a co-morbidity. For example, a user may specify that the user has previously been diagnosed with a disorder such as schizophrenia. Computing device 104 may obtain a second endocrinal measurement 148 relating to first endocrinal measurement 108. Computing device 104 may update dietary communication 128 as a function of second endocrinal measurement 148. This may be performed utilizing any of the methodologies as described above in more detail in reference to FIGS. 1-8.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random-access memory "RAM"

device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 9:
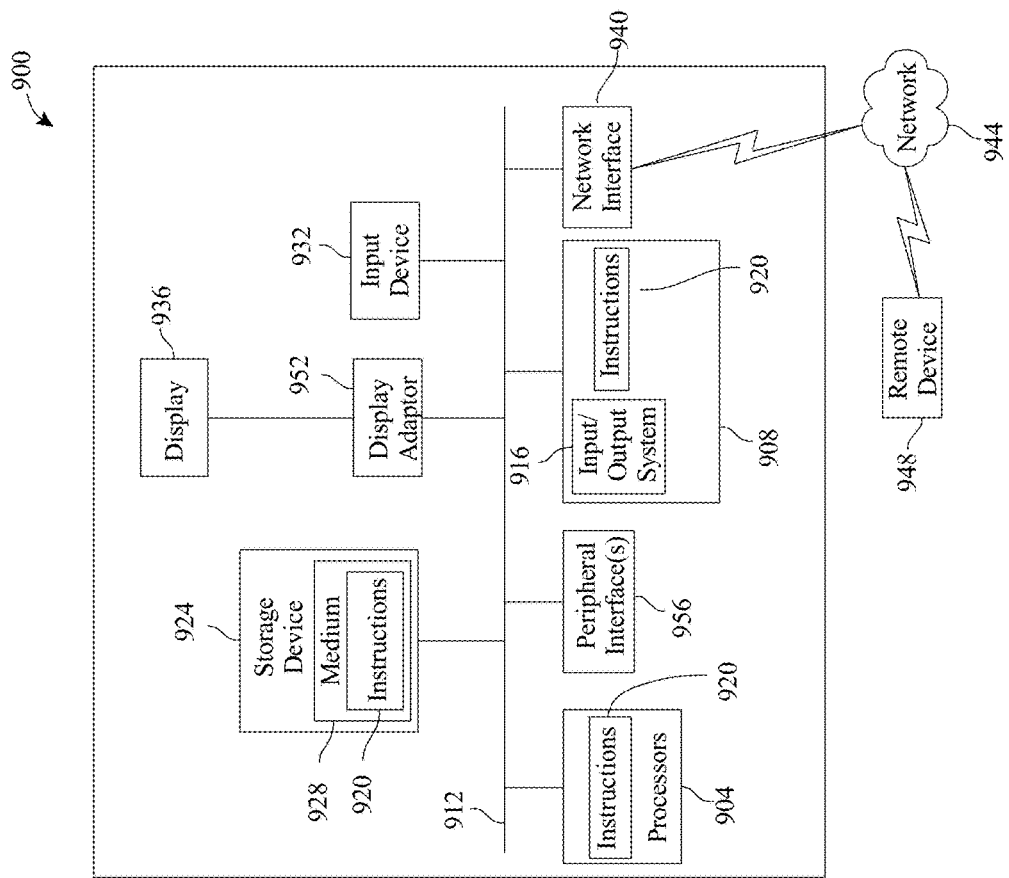
FIG. 9 is a block diagram of a computing system that can be used to implement any one or more of the methodologies disclosed herein and any one or more portions thereof.

FIG. 9 shows a diagrammatic representation of one embodiment of a computing device in the exemplary form of a computer system 900 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 900 includes a processor 904 and a memory 908 that communicate with each other, and with other components, via a bus 912. Bus 912 may include any of several types of bus structures including, but not limited to, a memory bus, a memory controller, a peripheral bus, a local bus, and any combinations thereof, using any of a variety of bus architectures.

Memory 908 may include various components (e.g., machine-readable media) including, but not limited to, a random-access memory component, a read only component, and any combinations thereof. In one example, a basic input/output system 916 (BIOS), including basic routines that help to transfer information between elements within computer system 900, such as during start-up, may be stored in memory 908. Memory 908 may also include (e.g., stored on one or more machine-readable media) instructions (e.g., software) 920 embodying any one or more of the aspects and/or methodologies of the present disclosure. In another example, memory 908 may further include any number of program modules including, but not limited to, an operating system, one or more application programs, other program modules, program data, and any combinations thereof.

Computer system 900 may also include a storage device 924. Examples of a storage device (e.g., storage device 924) include, but are not limited to, a hard disk drive, a magnetic disk drive, an optical disc drive in combination with an optical medium, a solid-state memory device, and any combinations thereof. Storage device 924 may be connected to bus 912 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 924 (or one or more components thereof) may be removably interfaced with computer system 900 (e.g., via an external port connector (not shown)). Particularly, storage device 924 and an associated machine-readable medium 928 may provide nonvolatile and/or volatile storage of machine-readable instructions, data structures, program modules, and/or other data for computer system 900. In one example, software 920 may reside, completely or partially, within machine-readable medium 928. In another example, software 920 may reside, completely or partially, within processor 904.

Computer system 900 may also include an input device 932. In one example, a user of computer system 900 may enter commands and/or other information into computer system 900 via input device 932. Examples of an input device 932 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 932 may be interfaced to bus 912 via any of a variety of interfaces (not shown) including, but not limited to, a serial interface, a parallel interface, a game port, a USB interface, a FIREWIRE interface, a direct interface to bus 912, and any combinations thereof. Input device 932 may include a touch screen interface that may be a part of or separate from display 936, discussed further below. Input device 932 may be utilized as a user selection device for selecting one or more graphical representations in a graphical interface as described above.

A user may also input commands and/or other information to computer system 900 via storage device 924 (e.g., a removable disk drive, a flash drive, etc.) and/or network interface device 940. A network interface device, such as network interface device 940, may be utilized for connecting computer system 900 to one or more of a variety of networks, such as network 944, and one or more remote devices 948 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus, or other relatively small geographic space), a telephone network, a data network associated with a telephone/voice provider (e.g., a mobile communications provider data and/or voice network), a direct connection between two computing devices, and any combinations thereof. A network, such as network 944, may employ a wired and/or a wireless mode of communication. In general, any network topology may be used. Information (e.g., data, software 920, etc.) may be communicated to and/or from computer system 900 via network interface device 940.

Computer system 900 may further include a video display adapter 952 for communicating a displayable image to a display device, such as display device 936. Examples of a display device include, but are not limited to, a liquid crystal display (LCD), a cathode ray tube (CRT), a plasma display, a light emitting diode (LED) display, and any combinations thereof. Display adapter 952 and display device 936 may be utilized in combination with processor 904 to provide graphical representations of aspects of the present disclosure. In addition to a display device, computer system 900 may include one or more other peripheral output devices including, but not limited to, an audio speaker, a printer, and any combinations thereof. Such peripheral output devices may be connected to bus 912 via a peripheral interface 956. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for dietary communications using intelligent systems regarding endocrinal measurements, the system comprising:
   a computing device designed and configured to:
   obtain a first endocrinal measurement relating to a user;
   compare the first endocrinal measurement to an endocrinal system effect;
   generate a body dysfunction label for the first endocrinal measurement as a function of the comparing to the endocrinal system effect;
   identify a dietary communication as a function of the body dysfunction label and the first endocrinal measurement, wherein identifying further comprises:
      receiving a first training set as a function of an expert database, wherein the first training set comprises the endocrinal measurements and the body dysfunction labels as inputs;
      training a first machine learning process as a function of the first training set relating endocrinal measurements and body dysfunction labels to output dietary communications; and
      identifying the dietary communication as a function of the body dysfunction label, the first endocrinal measurement, and the first machine-learning process, wherein the body dysfunction label and the first endocrinal measurement is an input to the first machine-learning process and the dietary communication is an output of the first machine-learning process;
   present the dietary communication on the computing device;
   obtain a second endocrinal measurement related to the first endocrinal measurement, wherein the second endocrinal measurement comprises an endocrinal measurement obtained subsequentially after the first endocrinal measurement;
   compare the second endocrinal measurement to a second endocrinal system effect;
   generate a second body dysfunction label for the second endocrinal measurement as a function of the comparing to the second endocrinal system effect;
   update the dietary communication as a function of the second body dysfunction label and the second endocrinal measurement, wherein identifying further comprises:
      receiving a second training set as a function of an expert database, wherein the second training set comprises the dietary communication of the first endocrinal measurement, first and second endocrinal measurements, and the body dysfunction labels of the first and second endocrinal measurement as inputs; and
      training a second machine learning process as a function of the second training set relating the dietary communication of the first endocrinal measurement, first and second endocrinal measurements and body dysfunction labels of the first and second endocrinal measurements to output an updated dietary communication;
      identifying the updated dietary communication as a function of the second machine-learning process; and
   present the updated dietary communication on the computing device.

2. The system of claim 1, wherein the first endocrinal measurement identifies a current endocrinal disorder.

3. The system of claim 1, wherein the first endocrinal measurement identifies a probable endocrinal disorder.

4. The system of claim 1, wherein the computing device is further configured to select the endocrinal system effect as a function of a user attribute.

5. The system of claim 1, wherein the computing device is further configured to:
   choose an individual input as a function of the body dysfunction label;
   receive an entry relating to the individual input from the user; and
   identify the dietary communications as a function of the individual input.

6. The system of claim 5, wherein the individual input is received from a wearable device.

7. The system of claim 5, wherein the individual input relates to a co-morbidity.

8. The system of claim 1, wherein the dietary communication contains restricted nutrients and allowed nutrients.

9. A method of dietary communications using intelligent systems regarding endocrinal measurements, the method comprising:
   obtaining, by a computing device, a first endocrinal measurement relating to a user; comparing, by the computing device, the first endocrinal measurement to an endocrinal system effect;
   generating, by the computing device, a body dysfunction label for the first endocrinal measurement as a function of the comparing to the endocrinal system effect;

identifying, by the computing device, a dietary communication as a function of the body dysfunction label and the first endocrinal measurement, wherein identifying further comprises:
  receiving a first training set as a function of an expert database, wherein the first training set comprises the endocrinal measurements and the body dysfunction labels as inputs;
  training a first machine learning process as a function of the first training set relating endocrinal measurements and body dysfunction labels to output dietary communications; and
  identifying the dietary communication as a function of the body dysfunction label, the first endocrinal measurement, and the first machine-learning process, wherein the body dysfunction label and the first endocrinal measurement is an input to the first machine-learning process and the dietary communication is an output of the first machine-learning process; and
presenting the dietary communication on the computing device:
obtaining, by the computing device, a second endocrinal measurement related to the first endocrinal measurement, wherein the second endocrinal measurement comprises an endocrinal measurement obtained subsequentially after the first endocrinal measurement;
comparing, by the computing device, the second endocrinal measurement to a second endocrinal system effect;
generating, by the computing device, a second body dysfunction label for the second endocrinal measurement as a function of the comparing to the second endocrinal system effect;
updating, by the computing device, the dietary communication as a function of the second body dysfunction label and the second endocrinal measurement, wherein identifying further comprises:
  receiving a second training set as a function of an expert database, wherein the second training set comprises the dietary communication of the first endocrinal measurement, first and second endocrinal measurements, and the body dysfunction labels of the first and second endocrinal measurement as inputs; and
  training a second machine learning process as a function of the second training set relating the dietary communication of the first endocrinal measurement, first and second endocrinal measurements and body dysfunction labels of the first and second endocrinal measurements to output an updated dietary communication;
  identifying the updated dietary communication as a function of the second machine-learning process; and
presenting the updated dietary communication on the computing device.

10. The method of claim 9, wherein the first endocrinal measurement identifies a current endocrinal disorder.

11. The method of claim 9, wherein the first endocrinal measurement identifies a probable endocrinal disorder.

12. The method of claim 9, wherein the endocrinal system effect is selected as a function of a user attribute.

13. The method of claim 9, wherein identifying the dietary communication further comprises:
  choosing an individual input as a function of the body dysfunction label; receiving an entry relating to the individual input from the user; and
  identifying the dietary communications as a function of the individual input.

14. The method of claim 13, wherein the individual input is received from a wearable device.

15. The method of claim 13, wherein the individual input relates to a co-morbidity.

16. The method of claim 9, wherein the dietary communication contains restricted nutrients and allowed nutrients.

* * * * *